United States Patent [19]

Marzoni

[11] Patent Number: 4,468,517

[45] Date of Patent: Aug. 28, 1984

[54] SYNTHESIS OF THIAZOLES

[75] Inventor: Gifford P. Marzoni, Indianapolis, Ind.

[73] Assignee: Eli Lilly and Company, Indianapolis, Ind.

[21] Appl. No.: 493,883

[22] Filed: May 12, 1983

[51] Int. Cl.³ .................. C07D 277/14; C07D 277/28
[52] U.S. Cl. .................................... 548/189; 544/133; 546/209; 548/202
[58] Field of Search ................ 548/202, 189; 544/133; 546/209

[56] References Cited

U.S. PATENT DOCUMENTS 3,391,151  7/1968  Davis ................................. 548/202

OTHER PUBLICATIONS

Hooper and Johnson, *J. Am. Chem. Soc.*, 56, 470–471, (1934).
Chi and Tshin, *J. Am. Chem. Soc.*, 64, 90–91, (1942).
Goldberg and Kelly, *J. Chem. Soc.*, 1372–1377, (1947).
Caldwell and Fox, *J. Am. Chem. Soc.*, 73, 2935–2936, (1951).

*Primary Examiner*—Robert Gerstl
*Attorney, Agent, or Firm*—Joseph A. Jones; Arthur R. Whale

[57] ABSTRACT

Certain 4-halomethylthiazoles having a 2-substituted-aminomethyl group are prepared by reacting an aminothioamide with a dihalopropanone in the presence of a haloalkane and a bicarbonate, and dehydrating the resulting intermediate.

20 Claims, No Drawings

SYNTHESIS OF THIAZOLES

BACKGROUND OF THE INVENTION

1. Field of the Invention

This invention belongs to the field of pharmaceutical chemistry, and provides a convenient process for the synthesis of certain thiazoles which are intermediates for the preparation of valuable anti-ulcer drugs.

2. State of the Art

Thiazoles have been prepared before by processes having a relationship to the present process. For example, Hooper and Johnson, working with barbituric acids in 1934, prepared a 2-methylthiazole by the reaction of 1,3-dichloropropanone and thioacetamide. *J. Am. Chem. Soc.* 56, 470–71 (1934). Brown and Dubarry, *Tet. Let.* 2797–98 (1969), made 4-chloromethyl-4-hydroxy-2-phenyl-2-thiazoline by reaction of thiobenzamide and 1,3-dichloropropane. Other reports in the literature show rather similar reactions to prepare 4-chloromethylthiazoles and 2-thiazolines. The usual conditions, however, reaction in an acid mixture, or in the presence of a strong base such as pyridine, are not effective to form the presently desired product, apparently because of the substituted aminomethyl group at the 2-position of those desired products.

SUMMARY OF THE INVENTION

The present invention provides a process for the synthesis of a 4-halomethylthiazole of the formula

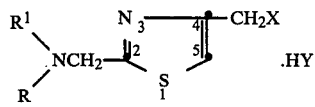
.HY wherein

X is bromo, chloro or iodo;

Y is a chlorine or bromine atom derived from the dehydrating agent; and

R and $R^1$ independently represent $C_1$–$C_3$ alkyl, or R and $R^1$ combine with the nitrogen atom to which they are attached to form pyrrolidino, piperidino or morpholino; which process comprises reacting a thioamide of the formula

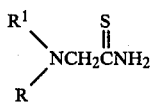

or a salt thereof,
with a dihalopropanone of the formula

wherein $X^1$ is bromo, chloro or iodo; in the presence of a haloalkane solvent and an alkali metal bicarbonate; to prepare a hydroxythiazoline intermediate of the formula

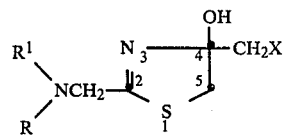

and dehydrating that intermediate with a chloro or bromo dehydrating agent chosen from $PCl_3$, $PBr_3$, $PCl_5$, $PBr_5$, $POCl_3$, $POBr_3$, $SO_2Cl_2$, $SOCl_2$ and $SOBr_2$.

DESCRIPTION OF THE PREFERRED EMBODIMENTS

All temperatures in the present document are described in degrees Celsius.

The term $C_1$–$C_3$ alkyl as used in the present document includes the groups methyl, ethyl, propyl and isopropyl.

It is believed that the compounds which are prepared by the present process are easily recognized by the skilled reader, but some typical products will be mentioned to assure full comprehension.

4-chloromethyl-2-dimethylaminomethylthiazole;
4-chloromethyl-2-ethylmethylaminomethylthiazole;
4-bromomethyl-2-dipropylaminomethylthiazole;
4-iodomethyl-2-isopropylmethylaminomethylthiazole;
4-chloromethyl-2-pyrrolidinomethylthiazole;
4-iodomethyl-2-piperidinomethylthiazole;
4-bromomethyl-2-morpholinomethylthiazole;
4-chloromethyl-2-ethylpropylaminomethylthiazole.

Certain groups of the products of the present process, and certain starting compounds used in it, are preferred. The following table lists preferred substituent groups which define such preferred products and starting materials. It will be understood that the preferred groups may be combined to define further, more limited groups.

A. X is chloro or bromo;
B. $X^1$ is chloro or bromo;
C. R is methyl or ethyl;
D. $R^1$ is methyl or ethyl;
E. X is the same as $X^1$;
F. X and $X^1$ are both chloro;
G. R is the same as $R^1$;
H. R and $R^1$ are both methyl.

The 4-chloromethyl products of the present process are used as intermediates, as taught by allowed U.S. patent application Ser. No. 319,155, filed Nov. 6, 1981. At page 17 of the typed specification, following flow chart A, it is explained that 4-chloromethylthiazoles are used as intermediates by reacting them with a sodium salt of the appropriate mercaptoalkylamine as the next step in the preparation of the pharmaceutical product, for example, the particularly preferred pharmaceutical nizatidine, of the following formula

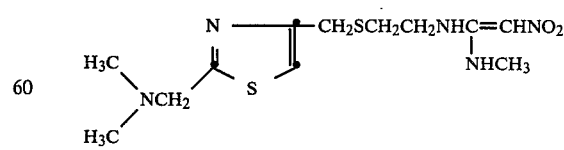

All of the starting compounds used in the present process are readily obtainable or easily prepared by the ordinarily skilled organic chemist.

The first step of the present process is the preferred step. In it, the dihalopropanone is reacted with the thioamide or a salt thereof, in the presence of an alkali metal bicarbonate, and in a haloalkane solvent. Sodium, potassium and lithium bicarbonates may be used as desired; sodium bicarbonate is preferred.

The thioamide starting compound can form acid addition salts which are also suitable reactants. For example, the hydrochloride, hydrobromide, sulfate, nitrate, phosphate, methanesulfonate, toluenesulfonate, oxalate, acetate, maleate, phosphonate, and like salts of the thioamide may be used freely as starting compounds.

The most preferred haloalkane solvent is 1,2-dichloroethane, but the various liquid haloalkanes may be used as desired, including 1,1,2-trichloroethane, 1,1-dibromomethane, 1,2-dibromoethane, 1,1-dichloroethane, dichloromethane, 1-chloro-2-bromoethane, chloroform, bromoform, carbontetrachloride and the like. It is not necessary for the reaction solvent to be pure haloalkane. Moderate amounts of other solvents may be used in the mixture as well, so long as the predominating portion of the reaction solvent is haloalkane. Such other solvents may be chosen from ketones, ethers and amides, such as acetone, methyl isobutyl ketone, tetrahydrofuran, diethyl ether, dimethylformamide, dimethylacetamide and the like. In general, about ⅔ or more of the volume of the reaction solvent should be haloalkane.

The concentration of the starting compounds in the reaction solvent is not important. It is unnecessary to use an appreciable excess of either starting compound, or of the base. A small excess, in the range of 1–10%, of the less expensive starting compound may advantageously be used to assure that the more expensive starting compound is fully utilized. It should be noted that an extra equivalent of the bicarbonate is needed in the reaction mixture when the thioamide is supplied in the form of a salt; otherwise, only one equivalent of bicarbonate is needed.

The first step of the process is carried out at a moderate temperature in the range of from about 0° to about 35°. It is preferable to carry out the first step at about the ambient temperature.

The first-step reaction is quite rapid, and its speed can cause difficulties if the reactants in a large-scale process are combined too quickly. It is preferable to add the bicarbonate and the thioamide to the reactor, and to add a solution of the dihalopropanone at a rate such that the evolution of gas is easily controlled and scrubbed.

When the first-step reaction is complete, or has gone as near to completion as the operator desires, the second-step reaction may be started by merely filtering the reaction mixture and adding the dehydrating agent to it, or adding it to the dehydrating agent. It is not necessary to purify or even to isolate the 4-hydroxy-2-thiazoline which is formed by the first step. On the other hand, it is entirely practical to isolate it, if it is desired to do so. It may be isolated by extracting it into water from the filtered haloalkane reaction solvent, but it is preferably isolated by the usual methods such as distilling the haloalkane from the mixture.

It should be noted, however, that the hydroxythiazoline intermediate is not particularly stable, and cannot be stored for more than a few days without unacceptable decomposition taking place. Accordingly, it is clearly preferred not to isolate the intermediate, but to use it immediately.

The dehydrating agent is chosen from the group consisting of phosphorous trichloride, phosphorous tribromide, phosphorous pentachloride, phosphorous pentabromide, phosphorous oxychloride, phosphorous oxybromide, sulfuryl chloride, thionyl chloride or thionyl bromide. It is preferred to use a dehydrating agent chosen from the chloro compounds just named, and most preferred to use sulfuryl chloride or thionyl chloride.

No particular excess of the dehydrating agent is needed, but, since those agents are comparatively inexpensive and easily obtained, it is advisable to use a moderate excess of them to assure complete consumption of the hydroxythiazoline.

It is preferred to carry out the second step at an elevated temperature, in the general range of from about the ambient temperature to about 100°. As usual in organic chemistry, the most convenient temperature is the ambient pressure reflux temperature of the reaction mixture, and the solvent in which the reaction is carried out may be adjusted to obtain the desired reflux temperature. Alternatively, the process may be operated under moderate pressure in order to raise the boiling temperature of the mixture.

As discussed above, it is preferred to carry out the second step in the reaction mixture from the first step. When the hydroxythiazoline is isolated, and a new reaction mixture prepared for the second step, any reaction solvent can be used that is not affected by the dehydrating agent. Ethers, haloalkanes, aromatics, haloaromatics, nitroaromatics, amides and ketones may be used as may be desirable in the individual case. Such solvents as acetone, methyl ethyl ketone, diethyl ether, tetrahydrofuran, dimethylacetamide, nitrobenzene, chlorobenzene, dichloromethane, toluene, xylene and the like may be used freely as the operator may choose.

The product of the present process is produced as a hydrahalide salt. When the dehydrating agent is a chloro compound, a hydrochloride is produced, and a hydrobromide is produced by a bromo dehydrating agent. The salt may be converted to the free base in a separate step, as usual, by treating the product with a strong base. There is no advantage to doing so, however.

The product of the present process is an intermediate and is used in further chemical steps. It has been found to be unnecessary to isolate the product; the reaction mixture at the end of the process may be used without further purification as the feed to the next synthetic step in the process, as shown below in Preparation 1. However, the product of the present process may be isolated by extracting it into water, or by filtering the precipitated product from the mixture.

The first group of examples following show the first step of the process of this invention, the formation of the hydroxythiazoline.

EXAMPLE 1

4-Chloromethyl-4-hydroxy-2-dimethylaminomethyl-2-thiazoline

To a flask were added 44.5 g. of dimethylaminothioacetamide, hydrochloride, 40.4 g. of 1,3-dichloropropanone, 224 ml. of 1,2-dichloroethane and 53.4 g. of sodium bicarbonate. An endothermic reaction took place and cooled the mixture to 13° on initial mixing. The mixture was then stirred overnight at ambient temperature, and the reaction was found to be essentially complete after 24 hours, by thin layer chromatography. The tlc system is silica gel, eluting with chloroform:methanol:ammonium hydroxide, 36:4:1. The mixture was then filtered, and the filter cake was washed with 1,2-dichloroethane. The filtrate was evaporated to dryness under vacuum to obtain 59.5 g. of crude product, which was washed with ethyl acetate. The washed solids were dried in air, to obtain 52.5 g. of substantially pure product, m.p. 90°–92°.

It was further identified by nuclear magnetic resonance analysis on a 60 mHz instrument in CDCl$_3$/DMSO-D$_6$, which showed characteristic features at δ2.3 (s, 6H); 3.1–3.7 (m, 4H); 3.8 (s, 2H).

EXAMPLE 2

4-Chloromethyl-4-hydroxy-2-dimethylaminomethyl-2-thiazoline

To a 100 ml. flask were added 10 g. of dimethylaminothioacetamide, hydrochloride, 9 g. of 1,3-dichloropropanone, 15 g. of potassium bicarbonate and 40 ml. of 1,2-dichloroethane. The mixture was stirred at ambient temperature for 24 hours, and was then filtered. The filtrate was evaporated to dryness under vacuum to obtain 12.3 g. of product, which was identified as substantially identical to the product of Example 1.

EXAMPLE 3

4-Chloromethyl-4-hydroxy-2-dimethylaminomethyl-2-thiazoline

A 2.4 g. portion of dimethylaminothioacetamide, 2.8 g. of 1,3-dichloropropanone and 1.9 g. of sodium bicarbonate were combined with 25 ml. of chloroform, and the mixture was stirred for 24 hours. The mixture was then filtered through a filter aid pad, and the filtrate was evaporated to dryness under vacuum to obtain 4.7 g. of impure product, which was analyzed by nuclear magnetic resonance and found to be substantially analytically identical to the product of Example 1. The product was noticeably more oily than that obtained in Examples 1 and 2.

EXAMPLE 4

4-Chloromethyl-4-hydroxy-2-dimethylaminomethyl-2-thiazoline

To a 50 ml. flask were added 1.2 g. of dimethylaminothioacetamide, 1.4 g. of 1,3-dichloropropanone and 0.9 g. of sodium bicarbonate, and 10 ml. of dichloromethane was added. The mixture was stirred for 16 hours at ambient temperature, and 20 ml. of dichloromethane and 30 ml. of water were added. The 2 phase mixture was stirred well, and the layers were separated. The aqueous layer was extracted twice with 20 ml. portions of dichloromethane and the organics were combined, dried over sodium sulfate and evaporated to dryness under vacuum to obtain 2.3 g. of product, which was analyzed by nuclear magnetic resonance methods and found to be substantially identical to the product of Example 1.

The following group of examples show the second step of the process, wherein the hydroxythiazoline is dehydrated.

EXAMPLE 5

4-Chloromethyl-2-dimethylaminomethylthiazole, hydrochloride

Ten g. of 4-chloromethyl-4-hydroxy-2-dimethylaminomethyl-2-thiazoline was dissolved in 50 ml. of 1,2-dichloroethane, and to it was added 8.6 g. of thionyl chloride dissolved in 30 ml. of 1,2-dichloroethane. The mixture was stirred at ambient temperature overnight, and then was stirred at 35° for 35 minutes and then for 1 hour at 50°. The mixture was cooled to 5° and filtered, and the solids were washed with 1,2-dichloroethane, and then were slurried in 20 ml. of methanol and 50 ml. of ethyl acetate. The crystals were then recovered by filtration and dried to obtain 6.4 g. of relatively pure product, m.p. 137°–140°. The product was identified by nmr analysis in DMSO-D$_6$, on a 60 mHz instrument, which analysis showed characteristic features at δ3.05 (s, 6H); 4.85 (s, 2H); 4.90 (s, 2H); 7.85 (s, 1H).

EXAMPLE 6

4-Chloromethyl-2-dimethylaminomethylthiazole, hydrochloride

Five g. of 4-chloromethyl-4-hydroxy-2-dimethylaminomethyl-2-thiazoline was added to 25 ml. of 1,2-dichloroethane, and 2.1 g. of sulfuryl chloride in 10 ml. of 1,2-dichloroethane was added. An exothermic reaction heated the mixture to 35° as soon as the addition began, so the mixture was cooled while the addition was made. The mixture was then stirred at ambient temperature for 1 hour, and was then heated to 42° for a short time. A 2-phase mixture formed, and the oily portion was removed and dissolved in 10 ml. of methanol. The methanol was removed under vacuum, and the residue was partially dissolved in 10 ml. of methanol, and then precipitated by addition of 25 ml. of ethyl acetate. The mixture was then cooled in the freezer, and the crystals were filtered off, washed with ethyl acetate and dried under vacuum at 30° to obtain 1.4 g. of the desired product, which was identified by nmr analysis as being substantially identical with the product of Example 5.

EXAMPLE 7

4-Chloromethyl-2-dimethylaminomethylthiazole, hydrochloride

A 1.9 g. portion of 4-chloromethyl-4-hydroxy-2-dimethylaminomethyl-2-thiazoline and 19 ml. of 1,2-dichloroethane were added to a 100 ml. flask, and the mixture was cooled while 1.53 g. of phosphorus oxychloride dissolved in 10 ml. of 1,2-dichloroethane was added dropwise. The mixture was stirred for 30 minutes at 23°, and then at 50° for 1 hour. It was cooled, and 25 ml. of water was added. The layers were separated, and both layers were examined by the tlc system described above in Example 1. No product or starting compound was in the organic layer. The aqueous layer contained all of the product and there was no indication of remaining starting material.

EXAMPLE 8

4-Chloromethyl-2-dimethylaminothiazole, hydrochloride

To a 50 ml. flask were added 20 ml. of 1,2-dichloroethane and 2.1 g. of 4-chloromethyl-4-hydroxy-2-dimethylaminomethyl-2-thiazoline. The mixture was cooled in an ice bath while 0.9 g. of phosphorus trichloride in 10 ml. of 1,2-dichloroethane was added dropwise. The ice bath was removed when the temperature of the mixture reached 15°, and the temperature reached 26° at the end of the addition. The mixture was then stirred at 25°–26° for 90 minutes, when tlc analysis showed only a trace of starting compound. The mixture was stirred for 3 days more. It was then filtered, and the solids were washed with 1,2-dichloroethane and dried under vacuum at 50° to obtain 3.3 g. of the desired product, which was identified by nmr analysis as being substantially identical to the product of Example 5.

EXAMPLE 9

4-Chloromethyl-2-dimethylaminomethylthiazole, hydrochloride

To a 100 ml. flask were added 2.1 g. of 4-chloromethyl-4-hydroxy-2-dimethylaminomethyl-2-thiazoline and 25 ml. of 1,2-dichloroethane. To the mixture was added dropwise a solution of 2.1 g. of phosphorous pentachloride and 50 ml. of 1,2-dichloroethane, while the temperature of the mixture was held in the range 17°–25°. After the addition, the mixture was stirred for 16 hours. It was then filtered, and the filter cake was washed with 1,2-dichloroethane and dried under vacuum at 50° to obtain 2.4 g. of the desired product, which was identified by nmr analysis as being substantially identical to the product of Example 5.

The following group of examples show processes in which the steps were carried out without isolation of the hydroxythiazoline.

EXAMPLE 10

4-Chloromethyl-2-dimethylaminomethylthiazole, hydrochloride

To a 500 ml. flask were added 260 ml. of 1,2-dichloroethane, 52.7 g. of dimethylaminothioacetamide, hydrochloride, 48.2 g. of 1,3-dichloropropanone and 63 g. of sodium bicarbonate. The mixture was stirred overnight, and was filtered. The filter cake was washed with 250 ml. of 1,2-dichloroethane, and the combined filtrates were added to a 1000 ml. flask and cooled in an ice bath. To it was added dropwise 30.7 ml. of sulfuryl chloride. The mixture was seeded with crystals of authentic product, and the mixture was allowed to warm to 30° and was stirred for 30 minutes after the addition was complete. It was then heated to 60° and stirred for 30 minutes more, and cooled to ambient temperature. It was then filtered, the filter cake was washed with 100 ml. of 1,2-dichloroethane, and it was blown dry with nitrogen. The solids were then dried under vacuum at 45° to obtain 75.3 g. of the desired product. The product was confirmed to be substantially identical to that of Example 5 by tlc analysis, using the system described above.

EXAMPLE 11

4-Chloromethyl-2-dimethylaminomethylthiazole, hydrochloride

To a 3-liter flask were added 1170 ml. of 1,2-dichloroethane, 308 g. of dimethylaminothioacetamide, hydrochloride, 279 g. of 1,3-dichloropropanone and 370 g. of sodium bicarbonate. The mixture was stirred for 8 hours, and 500 ml. of additional 1,2-dichloroethane was added and the mixture stirred for a short time more. It was then filtered, the filter cake was washed with 670 ml. of 1,2-dichloroethane, and the filtrates were combined and chilled in an ice bath. To the filtrate was added 157 ml. of thionyl chloride, dropwise, with good stirring. It was then warmed and stirred overnight at ambient temperature, and then for 30 minutes at 65°–70°. It was then cooled and filtered, and the solids were washed with 500 ml. of additional 1,2-dichloroethane and dried to obtain 427 g. of the desired product. The product was confirmed to be substantially identical to the product of Example 5 by nuclear magnetic resonance analysis.

EXAMPLE 12

4-Chloromethyl-2-dimethylaminomethylthiazole, hydrochloride

A mixture of 118 g. of dimethylaminothioacetamide, 92.4 g. of sodium bicarbonate, 140 g. of 1,3-dichloropropanone and 600 ml. of 1,2-dichloroethane was stirred at ambient temperature for 24 hours, and was then filtered. To the filtrate, at ice-bath temperature, was added 131 g. of thionyl chloride, dropwise. One hundred ml. of additional 1,2-dichloroethane was added, and the mixture was stirred for 2 hours at ambient temperature and then for 1 hour under reflux. The mixture was then chilled overnight, warmed to ambient temperature and filtered. The filter cake was washed with 200 ml. of 1,2-dichloroethane and blown dry, and the solids were dried overnight under vacuum to obtain 202.5 g. of the desired product, substantially identical to the product of Example 5.

EXAMPLE 13

4-Chloromethyl-2-dimethylaminomethylthiazole, hydrochloride

To a 1000 ml. flask were added 77 g. of dimethylaminothioacetamide, hydrochloride, 70 g. of 1,3-dichloropropanone, 92.4 g. of sodium bicarbonate and 350 ml. of 1,2-dichloroethane. The mixture was stirred at ambient temperature for 26 hours and filtered, and the filter cake was washed with 118 ml. of 1,2-dichloroethane. The filtrates were combined and cooled in an acetone-ice bath. To the filtrate was added, dropwise, 39.5 ml. of thionyl chloride at a temperature between 13° and 18°. The mixture was stirred at 20° for 30 minutes, then heated to 50°. An additional 100 ml. of 1,2-dichloroethane was added, and the mixture was stirred for 30 minutes at 60°. It was then cooled to ambient temperature, and 82 ml. of deionized water was added. The layers were separated, and the organic layer was extracted with 28 ml. and 14 ml. portions of deionized water. The aqueous layers were combined, and it was confirmed by tlc that the desired product had been collected in the aqueous layers.

Preparation 1

4-(2-Aminoethyl)thiomethyl-2-dimethylaminomethylthiazole

To the solution from Example 13 above was added 56.7 g. of 2-aminoethanethiol, hydrochloride. The mixture was then heated and stirred, and distilled. The distillation was stopped when the pot temperature reached 133°, after 22 ml. of organic and 115 ml. of aqueous distillate had been received. To the residue remaining in the distillation flask was added 100 ml. of deionized water, 100 ml. of dichloromethane, and 100 ml. of 50% aqueous sodium hydroxide, dropwise with ice bath cooling. The mixture was then filtered, and the filter cake was washed with dichloromethane. The aqueous layer of the filtrate was extracted twice with 100 ml. portions of dichloromethane, and then the organic layers were combined, dried over sodium sulfate and filtered. The filtrate was evaporated to dryness under vacuum to obtain 97.7 g. of the desired product, which was identified as being 79.8% pure by gas chromatography, using a 2 mm. by 6-foot column of Gaschrom-Q (Applied Science Co.) containing 10% of OV-210 (Ohio Valley Chemical Co.) using 25 ml./min. of helium as the carrier at 170° isothermal.

EXAMPLE 14

4-Chloromethyl-2-dimethylaminomethylthiazole, hydrochloride

To a flask were added 150 ml. of 1,2-dichloroethane, 38.5 g. of dimethylaminothioacetamide, hydrochloride, 34.9 g. of 1,3-dichloropropanone and 46.2 g. of sodium bicarbonate. The mixture was stirred at ambient temperature for 22 hours, and the mixture was filtered. The filter cake was washed with 50 ml. of 1,2-dichloroethane, and the combined filtrate was added dropwise to a solution of 20 ml. of thionyl chloride in 100 ml. of 1,2-dichloroethane. The temperature of the mixture was held at 20°-25° during the addition, and the mixture was stirred at ambient temperature overnight after the addition was complete. It was then heated to 65°-70° and held at that temperature for 30 minutes. To the reaction mixture was then added 75 ml. of water, and the mixture was stirred for 30 minutes before the layers were allowed to separate. The organic layer was then extracted with 38 ml. of deionized water, and then with 18 ml. of deionized water. All of the aqueous layers were combined, and examined by tlc, using the system described above, which showed that the aqueous phase contained the desired product.

Preparation 2

4-(2-Aminoethyl)thiomethyl-2-dimethylaminomethyl-thiazole

To the aqueous phase from Example 14 above was added 27 g. of 2-aminoethanethiol, hydrochloride. The mixture was heated and stirred, until the pot temperature reached 120°. The mixture was held at that temperature for 6 hours, and was then allowed to cool to 60°. To the residue was added 80 ml. of deionized water, and the mixture was allowed to cool to ambient temperature and stand for some days. Eighty ml. of dichloromethane was then added, and the pH of the mixture was adjusted to 6.1 by the addition of 9 ml. of 50% sodium hydroxide. The aqueous layer was extracted twice with 40 ml. portions of dichloromethane, and the aqueous layer was then mixed with 80 ml. of dichloromethane and the pH was adjusted to 12.6 by the addition of 40 ml. of 50% sodium hydroxide. The aqueous layer of the resulting mixture was extracted twice with 40 ml. of dichloromethane, and the two aqueous layers were combined, filtered and evaporated under vacuum to obtain 31.5 g. of the desired product, which was found to be 74.7% pure by the analytical method described in Preparation 1 above.

I claim:

1. A process for the synthesis of a 4-halomethyl-thiazole of the formula

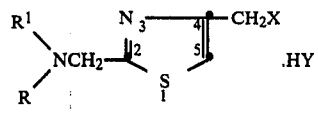

wherein
X is bromo, chloro or iodo;
Y is a chlorine or bromine atom derived from the dehydrating agent; and R and $R^1$ independently represent $C_1$–$C_3$ alkyl, or R and $R^1$ combine with the nitrogen atom to which they are attached to form pyrrolidino, piperidino or morpholino; which process comprises reacting a thioamide of the formula

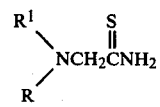

or a salt thereof,
with a dihalopropanone of the formula

wherein $X^1$ is bromo, chloro or iodo;
in the presence of a haloalkane solvent and an alkali metal bicarbonate; to prepare a hydroxythiazoline intermediate of the formula

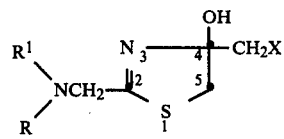

and dehydrating that intermediate with a chloro or bromo dehydrating agent chosen from $PCl_3$, $PBr_3$, $PCl_5$, $PBr_5$, $POCl_3$, $POBr_3$, $SO_2Cl_2$, $SOCl_2$ and $SOBr_2$.

2. A process of claim 1 wherein the product is a compound wherein R and $R^1$ are methyl or ethyl.

3. A process of claim 1 wherein the dihalopropanone is a compound wherein X and $X^1$ are chloro or bromo.

4. A process of claim 2 wherein the dihalopropanone is a compound wherein X and $X^1$ are chloro or bromo.

5. A process of claim 4 wherein the product is a compound wherein R and $R^1$ are methyl.

6. A process of claim 5 wherein the dihalopropanone is a compound wherein X and $X^1$ are chloro.

7. A process of claim 1 wherein the thioamide is reacted with the dihalopropanone at from about 0° to about 35°.

8. A process of claim 4 wherein the thioamide is reacted with the dihalopropanone at from about 0° to about 35°.

9. A process of claim 6 wherein the thioamide is reacted with the dihalopropanone at from about 0° to about 35°.

10. A process of claim 9 wherein the haloalkane is 1,2-dichloroethane and the alkali metal bicarbonate is sodium bicarbonate.

11. A process of claim 1 wherein the dehydrating agent is a chloro compound.

12. A process of claim 10 wherein the dehydrating agent is a chloro compound.

13. A process of claim 12 wherein the dehydrating agent is thionyl chloride or sulfuryl chloride.

14. A process of claim 13 wherein the hydroxythiazoline is not isolated.

15. A process for preparing a hydroxythiazoline of the formula

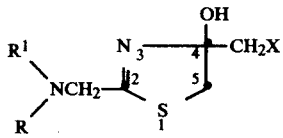

wherein
X is bromo, chloro or iodo; and
R and R$^1$ independently represent C$_1$–C$_3$ alkyl, or R and R$^1$ combine with the nitrogen atom to which they are attached to form pyrrolidino, piperidino or morpholino; which process comprises reacting a thioamide of the formula

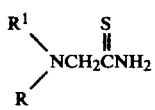

or a salt thereof,
with a dihalopropanone of the formula

wherein X$^1$ is bromo, chloro or iodo;
in the presence of a haloalkane solvent and an alkali metal bicarbonate.

16. A process of claim 15 wherein the product is a compound wherein R and R$^1$ are methyl or ethyl.

17. A process of claim 16 wherein the dihalopropanone is a compound wherein X and X$^1$ are chloro or bromo.

18. A process of claim 17 wherein the product is a compound wherein R and R$^1$ are methyl.

19. A process of claim 18 wherein the dihalopropanone is a compound wherein X and X$^1$ are chloro.

20. A process of claim 19 wherein the reaction is carried out at from about 0° to about 35°.

* * * * *